United States Patent
Miller et al.

(10) Patent No.: US 11,395,643 B2
(45) Date of Patent: Jul. 26, 2022

(54) LIQUID APPLICATOR

(71) Applicant: Advanced Medical Solutions Limited, Cheshire (GB)

(72) Inventors: Guy Stephen Miller, Plymouth (GB); Nithinkrishnan Gopalakrishnan, Plymouth (GB); Simon Mark Parish, Plymouth (GB)

(73) Assignee: ADVANCED MEDICAL SOLUTIONS LIMITED, Cheshire (GB)

(*) Notice: Subject to any disclaimer, the term of this patent is extended or adjusted under 35 U.S.C. 154(b) by 0 days.

(21) Appl. No.: 16/098,761

(22) PCT Filed: May 5, 2017

(86) PCT No.: PCT/GB2017/051260
§ 371 (c)(1),
(2) Date: Nov. 2, 2018

(87) PCT Pub. No.: WO2017/191470
PCT Pub. Date: Nov. 9, 2017

(65) Prior Publication Data
US 2019/0117208 A1    Apr. 25, 2019

(30) Foreign Application Priority Data

May 5, 2016  (GB) ..................... 1607868

(51) Int. Cl.
 A61B 17/00    (2006.01)
 A61L 24/06    (2006.01)
 A61B 90/00    (2016.01)
(52) U.S. Cl.
 CPC ........ *A61B 17/00491* (2013.01); *A61L 24/06* (2013.01); *A61B 2017/005* (2013.01);
(Continued)

(58) Field of Classification Search
CPC ........ A61B 17/00491; A61B 2017/005; B05B 1/00; B05B 1/34; B01F 13/0023; A61M 11/00; B05C 17/00516; A61L 24/06
See application file for complete search history.

(56) References Cited

U.S. PATENT DOCUMENTS 2,784,127 A    3/1957  Joyner et al.
3,527,224 A    9/1970  Rabinowitz
(Continued)

FOREIGN PATENT DOCUMENTS

CH    709 684    11/2015
EP    2 638 969    9/2013
(Continued)

OTHER PUBLICATIONS

International Search Report for PCT/GB2017/051260, dated Jul. 28, 2017 (3 pages).
(Continued)

*Primary Examiner* — Alexander J Orkin
(74) *Attorney, Agent, or Firm* — Nixon & Vanderhye P.C.

(57) ABSTRACT

A liquid applicator (1) for holding and discharging a curable liquid composition, comprises a receiver body (2) for holding a curable liquid composition, a discharge tip (20;30;40) having a longitudinal axis and further having a distal end remote from the receiver body (2) from which the liquid composition is discharged, and a discharge mechanism (5) for transferring liquid composition held by the applicator (1) to the tip (20;30;40) for discharge of the composition. The tip (20;30;40) comprises an outlet section (21d;31d;44d) having at least one groove formation (26;38;48) extending along the tip (20;30;40) to the distal end thereof. The applicator may be a surgical adhesive applicator.

17 Claims, 4 Drawing Sheets

(52) U.S. Cl.
CPC .......... *A61B 2017/0084* (2013.01); *A61B 2017/00522* (2013.01); *A61B 2017/00853* (2013.01); *A61B 2090/037* (2016.02)

(56) References Cited

U.S. PATENT DOCUMENTS

| | | | |
|---|---|---|---|
| 3,591,676 A | | 7/1971 | Hawkins et al. |
| 3,667,472 A | | 6/1972 | Halpern |
| 3,995,641 A | | 12/1976 | Kronenthal |
| 4,035,334 A | | 7/1977 | Davydov et al. |
| 4,444,933 A | | 4/1984 | Columbus et al. |
| 4,650,826 A | | 3/1987 | Waniczek et al. |
| 5,020,694 A | * | 6/1991 | Pettengill ............ B65D 81/325 222/137 |
| 5,116,315 A | * | 5/1992 | Capozzi ............ A61B 17/00491 222/137 |
| 5,312,333 A | * | 5/1994 | Churinetz ........ A61B 17/00491 604/140 |
| 5,322,510 A | * | 6/1994 | Lindner ............ A61B 17/00491 239/423 |
| 5,480,935 A | | 1/1996 | Greff et al. |
| 5,740,965 A | * | 4/1998 | Miyagi ............ A61B 17/00491 239/423 |
| 5,759,194 A | * | 6/1998 | Hammerslag .... A61B 17/00491 606/151 |
| 5,962,010 A | | 10/1999 | Greff et al. |
| 5,998,472 A | | 12/1999 | Berger et al. |
| 6,065,645 A | * | 5/2000 | Sawhney ............ B01F 5/0615 222/137 |
| 6,129,243 A | | 10/2000 | Pal et al. |
| 6,475,502 B1 | | 11/2002 | Lee et al. |
| 6,688,497 B2 | * | 2/2004 | Mehta .................. A61H 35/04 222/211 |
| 2001/0004692 A1 | | 6/2001 | Kidooka et al. |
| 2002/0176733 A1 | | 11/2002 | Clark et al. |
| 2003/0158527 A1 | * | 8/2003 | Mezzoli .................. B05B 1/34 604/275 |
| 2005/0042196 A1 | | 2/2005 | Askill et al. |
| 2006/0118580 A1 | * | 6/2006 | Spencer ............ B05C 17/00516 222/327 |
| 2008/0294099 A1 | | 11/2008 | Yatabe et al. |
| 2009/0112255 A1 | | 4/2009 | Leopold et al. |
| 2010/0114158 A1 | * | 5/2010 | Hattan ............ A61B 17/00491 606/214 |
| 2011/0027753 A1 | | 2/2011 | Maurat et al. |
| 2011/0082497 A1 | * | 4/2011 | Deslauriers ...... A61B 17/00491 606/213 |
| 2013/0072984 A1 | | 3/2013 | Robinson |
| 2013/0245576 A1 | * | 9/2013 | Hoogenakker ....... B05B 12/122 604/290 |
| 2015/0041559 A1 | | 2/2015 | Albisetti |
| 2015/0216516 A1 | * | 8/2015 | Steffen ............ A61B 17/00491 604/290 |

FOREIGN PATENT DOCUMENTS

| | | |
|---|---|---|
| GB | 2462136 | 2/2010 |
| JP | 9-989 | 1/1997 |
| JP | 2008-289986 | 12/2008 |
| JP | 2011-20031 | 2/2011 |
| JP | 5658544 | 1/2015 |
| WO | 2010/097896 | 9/2010 |
| WO | 2014/071395 | 5/2014 |
| WO | 2014/072688 | 5/2014 |
| WO | 2014/072689 | 5/2014 |

OTHER PUBLICATIONS

International Preliminary Report on Patentability issued in PCT/GB2017/051260 dated Nov. 6, 2018.

Search Report issued in GB Appln. No. 1607868.5 dated Oct. 27, 2016.

Office Action issued in JP App No. 2019-510480 (dated Feb. 9, 2021) (with translation).

Examination Report dated Nov. 8, 2021 issued in GB Application No. 1607868.5 (3 pages).

* cited by examiner

LIQUID APPLICATOR

This application is the U.S. national phase of International Application No. PCT/GB2017/051260 filed May 5, 2017 which designated the U.S. and claims priority to GB 1607868.5 filed May 5, 2016, the entire contents of each of which are hereby incorporated by reference.

The present invention relates to a liquid applicator for holding and discharging a curable liquid composition. The invention relates particularly, but not necessarily exclusively, to such applicators intended for surgical use for successive delivery of droplets of the curable liquid composition to a surgical site. The invention has particular (but again not exclusive) application to applicators for laparoscopic surgery for the repair of hernias by fixing a mesh support material to the tissue being repaired.

Liquid applicators which are for use in laparoscopic surgery (e.g. hernia repair operation) and which function by successive delivery of droplets (e.g. 12-15 µl/droplet) are known in the art. An example of such an applicator is disclosed in WO 2014/072688 and WO2014/072689. A commercially available applicator (operating in accordance with the principles disclosed in the two aforementioned WO specifications) is available from Advanced Medical Solutions (Plymouth) under the name LIQUIBAND®FIX8™ and delivers droplets of a curable liquid cyanoacrylate adhesive composition. The FIX8 device is intended for use in a single surgical operation and is configured to deliver a total of about 33 droplets of adhesive, sufficient for one hernia mesh fixation operation. Cyanoacrylate is however known to interfere with natural healing at the immediate point of contact and so, for internal applications, it has been found that controlling and minimising the amount of adhesive applied is critical. To this end, liquid applicators for internal surgical use (e.g. the FIX8™ device) have outlet tips with small diameter bores (e.g. about 0.5-2.0 mm). However due to the high moisture content of internal tissues there is a significant risk of the tip becoming blocked with polymerised material for one or both of two reasons. Firstly, polymerised material and tissue may build up on the outside of the tip covering the distal orifice (i.e. the orifice from which the adhesive composition is discharged onto the surgical site). Secondly, polymerised material and tissue can form inside the distal orifice causing a plug. If blockage occurs the applicator may no longer be suitable for use in completing the surgical procedure.

It is an object of the present invention to obviate or mitigate the abovementioned disadvantages.

According to the present invention there is provided a liquid applicator for holding and discharging a curable liquid composition, the applicator comprising:
  a receiver body for holding a curable liquid composition,
    a discharge tip having a longitudinal axis and further having a distal end remote from the receiver body from which the liquid composition is discharged, and a discharge mechanism for transferring liquid composition held by the applicator to the tip for discharge of the composition,
  wherein the tip comprises an outlet section having at least one groove formation extending along the tip to the distal end thereof.

The invention further provides a liquid applicator as defined in the previous paragraph charged with a curable liquid adhesive composition, e.g. contained in a frangible curable liquid adhesive composition, e.g. contained in a frangible ampoule that needs to be fractured to release the adhesive composition for discharge.

The liquid applicator may be configured as a surgical instrument, e.g. for use in a hernia mesh fixation operation.

We have found that the provision of at least one groove formation in an outlet section of the tip and extending therealong to the distal end thereof considerably reduces problems associated with blockage. There may be a single groove formation provided either internally or externally of the tip and having a longitudinal axis parallel to that of the tip. Preferably however a plurality of internal or external groove formations, e.g. four, are provided and have their longitudinal axes equiangularly spaced around the longitudinal axis of the tip.

In a particularly preferred embodiment of the invention, the tip has a bore extending through the tip to the distal end thereof and groove formations are formed in the interior wall of the bore. The bore of the tip may have an upstream section of constant cross-section (e.g. 1.5-2 mm) and a downstream section in which the groove formations are provided. The groove formations may, for example, extend for a length of 4 to 6 mm (preferably about 5 mm).

It is particularly preferred that the upstream ends of the groove formations are defined by shoulders lying in a plane at right-angles to the direction of flow of the liquid composition through the tip.

Preferably the groove formations formed internally of the bore of the tip are of arcuate (preferably semi-circular) when seen in transverse section (i.e. the plane at right angles to the direction flow of the liquid composition through the tip).

In an alternative embodiment of the invention, the tip has an upstream section provided with a bore and a downstream section (providing the outlet section) in the exterior of which the groove formations are provided. In this embodiment, the grooves are each associated with an aperture providing communication between a groove and the bore (which extends no further than said apertures). The apertures may be provided at least partly in the base of each groove formation and are preferably arcuate (as seen in transverse cross-section) with each aperture extending partly up the arcuate side walls of the grooves.

For all embodiments of the invention, it is preferred that the tip comprises a low surface energy material as such materials serve to minimise adhesion of cured adhesive composition and debris to the tip. The low surface energy material from which the tip is fabricated may, for example, comprise high density polyethylene, polypropylene, fluorinated polymer (e.g. PTFE), an acetal plastics material, silicones or a ceramic material.

The applicator is preferably one adapted to deliver successive droplets of curable liquid composition, e.g. by virtue of a trigger mechanism configured to effect the successive discharge. The droplets may have a volume of 10-20 µl, (e.g. 12-15 µl) and the device may be configured for delivery of 25-40, e.g. 30-35, droplets of adhesive.

The applicator may comprise an elongate cannula through which the adhesive composition is discharged and at the end of which the tip is mounted. For this purpose, the tip may comprise an upstream body portion and a downstream body portion of lower cross-sectional size than the former. The upstream body portion may therefore be in the form of a spigot for location in the end of the cannula with a shoulder (formed at the junction of the upstream and downstream body portions) abutting against the end of the cannula. The upstream and downstream body portions may for example be of circular cross-section. In preferred embodiments of the invention, the cannula incorporates an inner tube (e.g. of a fluorinated polymer such a PTFE) along which the adhesive composition is fed from the body of the applicator to the tip.

This inner tube preferably extends into the tip and preferably terminates before the outlet end thereof.

The applicator is preferably one configured for laparoscopic surgical use. It will however be appreciated that applicators in accordance with the invention may be used for open surgery.

In the applicator configured for surgical use, the tip may, for example, have an overall length of 15-25 mm (e.g. 18-24 mm) and/or a maximum cross-sectional dimension of 3-8 mm (e.g. 4-6 mm). If sub-divided into upstream and downstream body portions, the subdivision may be about midway along the length of the tip. The bore that extends into the tip from the upstream end thereof (and which feeds the adhesive composition to the groove formations) may optionally have a converging inlet section (for insertion of the aforementioned inner tube) but otherwise be of uniform, cross-section to the point where it communicates with the upstream ends of the groove formations. Other cross-sections may however be employed, e.g. the bore may narrow in cross-section part-way along its length at a converging step formation before it reaches the upstream ends of the groove formations. Apart from a converging inlet section, the bore may, for example, have a maximum cross-sectional size of 1.5 to 3.5 mm.

In the embodiments as described above, the groove formations may, for example, have a length of 4-8 mm. In the case where the groove formations have an arcuate (e.g. semi-circular section) then the radius of that section may, for example, be 0.3 to 1 mm (e.g. 0.4 to 0.8 mm). As viewed is transverse cross-section of the tip (i.e. in a plane intersected at right angles by the longitudinal axis of the tip) the centres of the arcuate sections may be 0.75 mm to 1.5 mm from the longitudinal axis of the lip. The or each groove formation preferably has a longitudinal axis that extends parallel to the longitudinal axis of the tip.

A liquid adhesive applicator in accordance with the invention intended for surgical use is ideally such that there is no substantial polymerisation (curing) of the adhesive before it reaches the end of the tip so that curing occurs when the adhesive comes into contact with the moisture of tissue being repaired. As such, it is preferred that there are no polymerisation initiators pre-deposited on the tip upstream of the outlet end thereof (such as are provided in certain other types of applicators of curable adhesive compositions).

The curable liquid composition is preferably a cyanoacrylate adhesive composition.

Examples of cyanoacrylate adhesive compositions that may be incorporated in the applicator are given below.

The adhesive fluids that may be applied by the applicator of the present invention may be comprised of a wide variety of cyanoacrylate adhesive formulations. The reservoir may contain a stronger bonding and less flexible cyanoacrylate adhesive composition, such as n-butyl cyanoacrylate, or it may contain a more flexible tissue adhesive, such as an octyl or hexyl or decyl or other homologs of cyanoacrylate.

Preferably, the cyanoacrylate compositions used comprise cyanoacrylate prepolymer compositions that can be applied as a liquid/gel to the skin surface. Optionally, the cyanoacrylate prepolymers can include therapeutic agents such as analgesics, anti-inflammatory agents, antimicrobial agents, and the like.

Preferably, the polymerizable cyanoacrylate prepolymers comprise cyanoacrylate esters that, in monomeric form, are represented by the formula I:

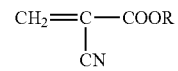

wherein
R is selected from the group consisting of:
alky of 1 to 10 carbon atoms,
akenyl of 2 to 10 carbon atoms,
cycloalky groups of from 5 to 8 carbon atoms,
phenyl,
2-ethoxyethyl,
3-methoxybutyl,
and a substituent of the formula:

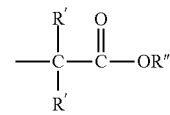

wherein
each R' is independently selected from the group consisting of:
hydrogen and methyl, and
R" is selected from the group consisting of:
alkyl of from 1 to 6 carbon atoms,
alkenyl of from 2 to 6 carbon atoms,
alkynl of from 2 to 6 carbon atoms,
cycloalkyl of from 3 to 8 carbon atoms,
aralkyl selected from the group consisting of benzyl, methylbenzyl and phenylethyl,
phenyl, and phenyl substituted with 1 to 3 substituents selected from the group consisting of hydroxyl, chloro, bromo, nitro, alkyl of 1 to 4 carbon atoms, and alkoxy of from 1 to 4 carbon atoms.

More preferably, in the cyanoacrylate esters of formula I, R is an alkyl group of from 2 to 10 carbon atom including ethyl, n-propyl, iso-propyl, n-butyl, iso-butyl, sec-butyl, n-pentyl, iso-pentyl, n-hexyl, 2-ethylhexyl, n-heptyl, octyl, nonyl, and decyl. Mixtures of such compounds can also be employed as disclosed by Berger, et al., U.S. Pat. No. 5,998,472, which is incorporated herein by reference in its entirety.

It is to be understood that the term "polymerizable cyanoacrylate esters" refers to polymerizable formulations comprising cyanoacrylate monomers or polymerizable oligomers which, in their monomeric form, are preferably compounds represented by formula I as described above.

The polymerizable cyanoacrylate esters described herein rapidly polymerize in the presence of water vapour or tissue protein, and the n-butyl-cyanoacrylate bonds to mammalian skin tissue without causing histotoxicity or cytotoxicity.

Polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

Optionally, the cyanoacrylate compositions applied by the present applicator can include a "biocompatible plasticizer". As used herein, the "biocompatible plasticizer" refers to any material which is soluble or dispersible in the cyanoacrylate composition, which increases the flexibility of the resulting polymeric film coating on the skin surface, and which, in the amounts employed, its compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and $C_2$-$C_4$-acyl tri-n-hexyl citrates.

Optionally as well, the cyanoacrylate composition applied by the present applicator can include an "antimicrobial agent". As used herein, the term "antimicrobial agent" refers to agents which destroy microbes (i.e. bacteria, fungi, yeasts and viruses) thereby preventing their development and their pathogenic action.

Preferred cyanoacrylate compositions useful in the practice of this invention are also disclosed by Greff, et al., U.S. Pat. No. 5,480,935, which application is incorporated herein by reference in its entirety. In a particularly preferred embodiment, the cyanoacrylate adhesive composition further comprises an antimicrobially effective amount of compatible antimicrobial agent. Such compositions preferably comprise from 0.1 to about 30 and preferably about 0.5 to 10 weight percent of the compatible antimicrobial agent either as a solution or as suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin. Suitable such compositions are disclosed in U.S. Pat. No. 6,475,502, which discloses compositions of cyanoacrylate/povidone-iodine complexes, and US 2005-0042196 A1, which discloses compositions of cyanoacrylate esters and phenol. All three disclosures are incorporated herein by reference in their entirety.

The use of compatible antimicrobial agent in the compositions permits the agent to be released from the polymeric film thereby reducing microbial growth adjacent to the film.

Other medicaments suitable for use in conjunction with the cyanoacrylate compositions include corticoid steroids such as described by Greff, et al. in U.S. Pat. No. 5,962,010 which is incorporated herein by reference in its entirety and analgesic compounds such as lidocaine. The former reduces inflammation whereas the latter reduces pain. Combinations of a steroid with an analgesic are also covered.

The invention will be further described, by way of example only, with reference to the accompanying drawings, in which.

Figure 1:
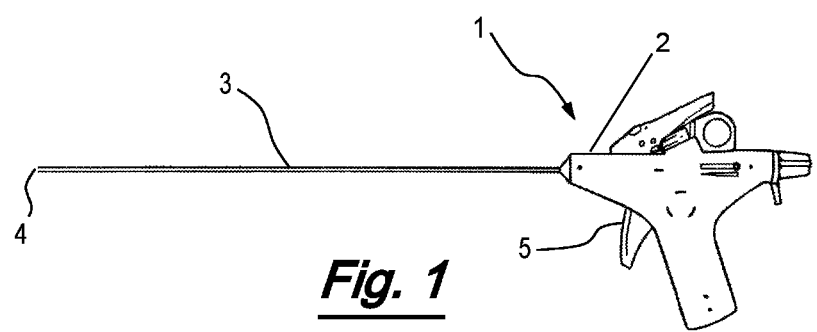
FIG. 1 shows a commercially available surgical adhesive applicator.

Illustrated in FIG. 1 is an adhesive applicator 1 sold by Advanced Medical Solutions (Plymouth) Ltd under the trade mark "LIQUIBAND™ FIX8™" for use in fixing a support mesh (usually of polypropylene) in place during a hernia repair operation, particularly such an operation effected laparoscopically. The "LIQUIBAND® FIX8™" device is intended for use in a single hernia repair operation during which a plurality of drops of curable cyanoacrylate adhesive composition are selectively and successively discharged to fix the mesh in position. The illustrated applicator 1 is of the type disclosed in WO 2014/072688 and WO 2014/072689 the disclosure of which is hereby incorporated by reference and to which reference may be made for full details as to the manner in which the applicator 1 is constructed and operated. However, in brief, applicator 1 comprises a body unit 2, an elongate cannula 3 extending from the body unit 2 and provided at its free distal end with an applicator tip 4, and further provided with a trigger mechanism 5. Although not illustrated in FIG. 1, cannula 3 has a liner tube of a fluorinated polymer which extends along cannula 3 from its proximal end within body unit 2 into the bore of the applicator tip 4 to a position level with the free distal end of tip 4. As supplied, the FIX8™ device includes in the body unit 2 thereof a frangible ampoule (not shown) containing a liquid adhesive composition incorporating a curable cyanoacrylate adhesive composition which is curable on contact with patient tissue to which the aforementioned support mesh is to be adhered. Provided on and within the body unit 2 are mechanisms which allow the ampoule to be fractured to release the adhesive and then to allow the cannula 3 (or more specifically the fluorinated liner tube) to be primed more-or-less along its full length with adhesive so that operation of the trigger mechanism 5 allows (for each such operation) discharge from the tip 4 of a droplet of liquid adhesive of a fixed volume (about 10-15 µl). The amount of adhesive supplied with the FIX8™ applicator is sufficient for discharge of about 33 droplets of adhesive.

During a hernia repair operation, the aforementioned mesh is located in position against the patient's internal tissue to be repaired and droplets of adhesive (discharged as briefly described above by operation of trigger mechanism 5) are applied to the junctions of the mesh (on the side remote from patient tissue) so that adhesive can flow over the junction and into contact with the tissue (to form an adhesive "anchor") and cure, whereby the mesh becomes bonded to the tissue.

Figure 2:
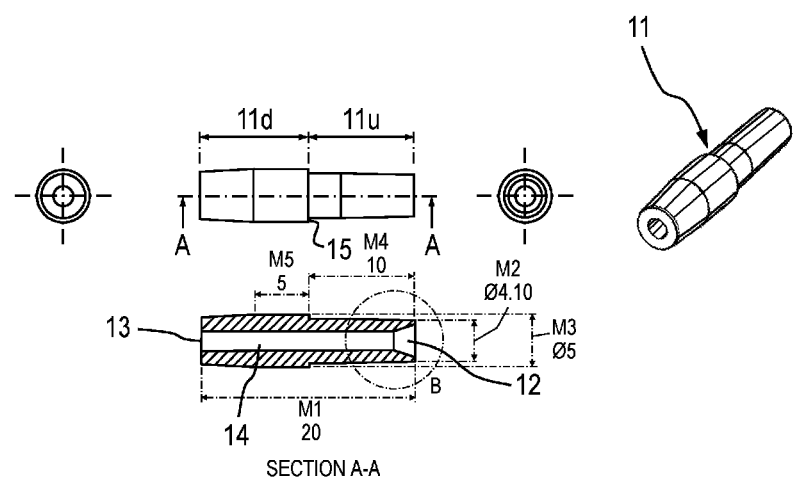
FIG. 2 shows views of a conventional applicator tip as supplied with the applicator shown in FIG. 1.

The tip 4 currently supplied with the FIX8™ device is shown in FIG. 2 and will be seen to comprise a tubular body 11 with an inwardly converging inlet 12 and an outlet 13 connected by a bore 14 which is of uniform, circular cross-section along its length from the downstream end of converging inlet 12 to the outlet 13. The provision of the inwardly converging inlet 12 facilitates insertion of the aforementioned fluorinated liner tube into the tip 4.

Body 11 is provided approximately mid-way along its length with an external annular shoulder 15 which subdivides body 11 into upstream and downstream sections 11u and 11d respectively. Upstream section 11u is for location within the distal end of cannula 3 such that annular shoulder 15 abuts against the distal end of cannula 3 with the downstream end 11d projecting beyond the end of cannula 3.

Tip 4 as supplied with the FIX8™ device has the dimensions shown in Table 1 below.

TABLE 1

| | |
|---|---|
| Length of body 11 | 20 mm |
| Length of upstream section 11u | 10 mm |
| Length of downstream section 11d | 10 mm |
| Outside diameter of upstream section 11u | 5 mm |
| Height of shoulder 15 | 0.9 mm |
| Diameter of bore 14 | 1.85 mm |

As indicated in Table 1, bore 14 has an internal diameter of about 1.85 mm. This allows small quantities of adhesive to be applied (about 13 μl with each activation of the trigger mechanism 5), which is advantageous since cyanoacrylate is known to interfere with natural healing at the immediate point of contact with patient tissue. Therefore, for internal applications, it has been found that controlling and minimising the amount of adhesive applied is critical. However, due to the high moisture content of internal tissues, coupled with the narrow diameter of bore 14, issues arise with the interior of the tip becoming blocked with polymerised cyanoacrylate material (and also polymerised cyanoacrylate around the exterior of the distal end of the tip 4). If the blockage cannot be cleared then the applicator cannot be used for further application of adhesive.

Figure 3:
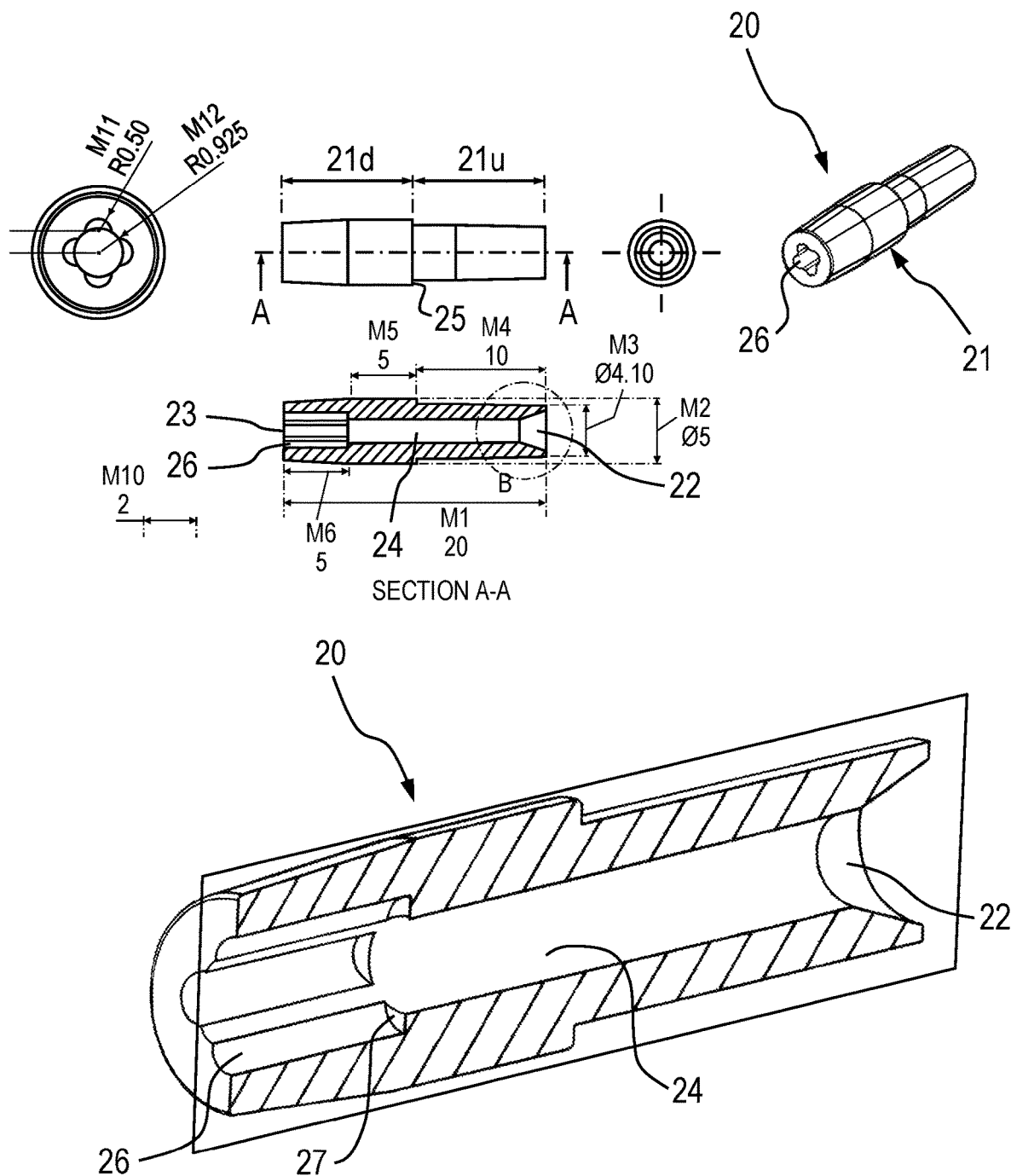
FIG. 3 shows views of a first embodiment of applicator tip for use in accordance with the invention.

Reference is now made to FIG. 3 which illustrates an embodiment of tip 20 which is for use in an applicator in accordance with the invention and which has been found significantly to reduce problems associated with blockage from polymerised cyanoacrylate. Thus, for example, tip 20 may be used in the FIX8™ device in place of the tip 4 described with reference to FIG. 2. The illustrated tip 20 has some general similarity with tip 4 and as such comprises a generally tubular body 21 having an inwardly converging inlet 22 and an outlet 23 connected by a bore 24 that extends from the downstream end of inwardly converging inlet 22 to the outlet 23. Body 21 is provided with an external annular shoulder 25 which, in effect, sub-divides body 21 into upstream and downstream sections 21u and 21d whereof the former is of lower external diameter than the latter. Upstream body section 21u locates in the distal end of cannula 3 with the shoulder 25 locating against the distal end of cannula 3.

Formed in the wall of the bore 24 are four axially parallel, equiangularly spaced grooves 26 that extend from a location about halfway along downstream body section 21d to the outlet 23. More specifically, the groves 26 extend in the downstream direction (to the outlet 23) from respective upstream end faces 27 formed as a result of the grooves 26 being moulded in the walls of block 24. Grooves 26 are generally semi-circular as seen in transverse cross-section (i.e. in a plane at right angles to the longitudinal axis of tip 20) and their configuration is best seen in the cut-away sectional view (which is to a much enlarged scale) in the lowermost drawing of FIG. 3.

Tip 20 may have the dimensions shown in Table 2 below.

TABLE 2

| | |
|---|---|
| Length of body 21 | 20 mm |
| Length of upstream section 21u | 10 mm |
| Length of downstream section 21d | 10 mm |
| Outside diameter of upstream section 21u | 5 mm |
| Height of shoulder 25 | 0.9 mm |
| Diameter of bore 24 | 1.85 mm |
| Lengths of grooves 26 | 5 mm |
| Radius of grooves 26 | 0.5 mm with centre positioned 0.8 mm from centre of distal tip |

Figure 4:
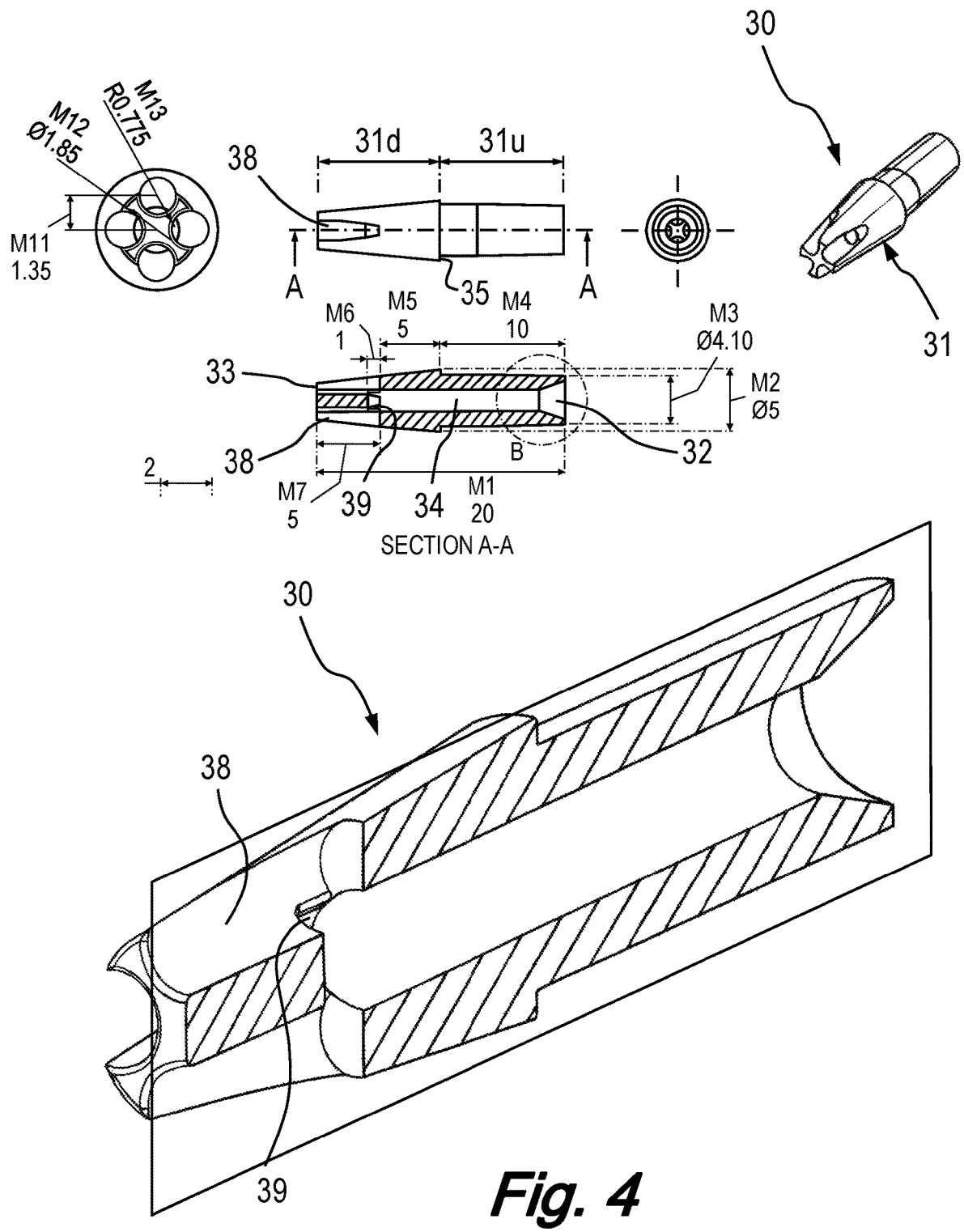
FIG. 4 shows views of a second embodiment of applicator tip for use in accordance with the invention.

FIG. 4 illustrates a further embodiment of tip 30 that may be used in an applicator in accordance with the invention to alleviate the above described blockage problems. Tip 30 has some similarity in overall construction with tip 20 and therefore, for convenience parts in tip 30 that have a counterpart in tip 20 are designated by a reference with the same final numeral and ten more than the corresponding numeral in FIG. 3. Thus, for example, the body of tip 30 is referenced as 31 (cf body 21 of tip 20). Also, for convenience, description of the like parts is not repeated.

In contrast with the embodiment of applicator tip 20 illustrated in FIG. 3, the applicator tip 30 is provided with external grooves 38 extending parallel to the longitudinal axis of tip 30 and being open along their length at the outer surface of tip 30. Each groove 38 is generally arcuate in transverse cross-section and extends between the distal end 33 of tip 30 and a respective wall 39 at the upstream end of groove 38. Over their lengths, the upper edges of grooves 38 rise slightly in going from distal end 33 to wall 39 whereby the grooves 38 increase in depth in going in this direction. Formed in the base of each groove 38 at the upstream end thereof (and extending part way up the lateral surfaces of the grooves) are respective apertures 39 that provide communication with the bore 34, which in this embodiment extends from the downstream end of inwardly converging inlet section 34 to the downstream ends of apertures 38. Thus, when tip 30 is located in the end of cannula 3 of applicator 1 and the applicator is primed with adhesive, operation of trigger mechanism 5 causes adhesive to pass into bore 34 of tip 30 and then via apertures 39 into the grooves 38 for discharge from tip 30.

Tip 30 may have the dimensions shown in Table 3 below.

TABLE 3

| | |
|---|---|
| Length of body 31 | 20 mm |
| Length of upstream section 31u | 10 mm |
| Length of downstream section 31d | 10 mm |
| Outside diameter of upstream section 31u | 5 mm |
| Height of shoulder 35 | 0.9 mm |
| Diameter of bore 34 | 1.85 mm |
| Lengths of grooves 38 | 5 mm |
| Radius of grooves 38 | 0.75 mm radius with the centre positioned 1.3 mm from the centre of the distal tip |

Figure 5:
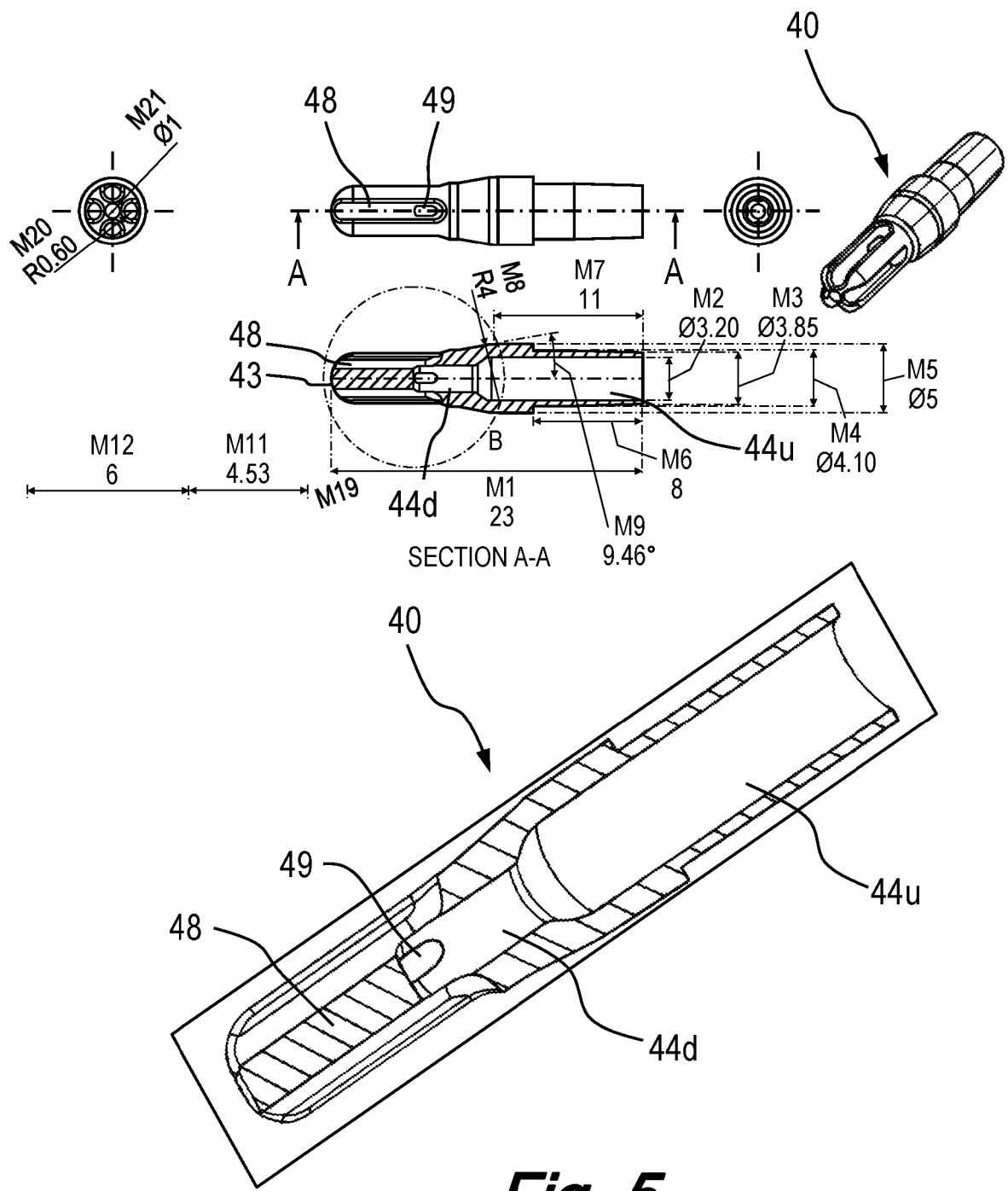
FIG. 5 shows views of a third embodiment of applicator tip for use in accordance with the invention.

A further embodiment of tip 40 is illustrated in FIG. 5 and, like tip 30 shown in FIG. 4, is provided with external grooves referred as 48, although in this case the grooves 48 are of constant depth along their length is going from distal end 43 of tip 40 to end face 49. Tip 40 includes a stepped bore shown as having an upstream section 44u and narrower downstream section 44d which extends a short distance beyond the upstream ends of grooves 48. Provided on the base of each groove 48 of the upstream end is a respective aperture 39 providing communication between a groove 38 and the downstream section 44d of the bore.

Tip 4 may have the dimensions shown in Table 4 below.

TABLE 4

| | |
|---|---|
| Length of body 41 | 23 mm |
| Diameter of upstream bore section 44u | 3.2 mm |
| Diameter of downstream bore section 44d | 4.53 mm |
| Lengths of grooves 48 | 7.68 mm |
| Radius of grooves 48 | 0.6 mm with the centre positioned 1.35 mm from the centre of the distal tip |

To demonstrate the effectiveness of the invention, samples of tips as shown in FIGS. 2-5 and having the dimensions indicated in the respective Tables above were manufactured from PTFE and further samples were manufacture from a Class VI acetal plastics material (Delrin®). The various tips were tested for their blockage characteristics using a test rig reliably simulating the delivery characteristics of the FIX8 device (repeated delivery of ca 13 µl droplets of a curable cyanoacrylate adhesive composition as supplied with the device). In all tests, the adhesive composition was delivered to the tips through a fluorinated polymer tube of the type used in the FIX8 device. The tube was inserted into the upstream end of the tip and extended to a position 5 mm from the discharge end of the tip.

The tests involved bonding a polypropylene mesh (of the type used in a hernia fixation operation) to chicken tissue using the various tips at angles of 90° to the horizontal (i.e. tip pointing vertically downwards), 60° to the horizontal (tip inclined downwardly), and 75° to the vertical (tip inclined upwards).

For each tip at each angle, the test was conducted using the following procedure.

(A) An adhesive anchor (provided by a droplet of adhesive) was expressed on to the mesh/chicken tissue surface.

(B) After each anchor application, the mesh was pushed and held in place using the tip for 10 seconds.

(C) After a wait of 20 seconds, the next adhesive anchor was deployed.

(D) The rate of adhesive delivery was such that at least 5 anchors were delivered within 2 minutes.

(E) The tip was observed for blockage due to debris accumulation after each adhesive anchor delivery.

(F) After deployment of every 3 adhesive anchors, the tip was subjected to the moist surface on the chicken tissue for 10 seconds.

(G) Steps (A)-(F) were repeated until at least 33 anchors had been expressed onto the mesh/chicken sample or until tip blockage (whichever occurred earlier).

As a result of the tests, it was found that tips of the type shown in FIG. 2 and made from either PTFE or acetal plastics material were prone to blockage that could not be cleared before 33 anchors had been expressed.

The tip shown in FIG. 3 and made of acetal plastics material provided the best results of all tips tested and was able to deliver adhesive composition for the required minimum of 33 anchors even though debris had accumulated around the tip. In the case of the tip of FIG. 3 made from PTFE, accumulated debris blocked the tip but the block was clearly visible and could easily be removed to restore the flow of adhesive to allow expression of the minimum 33 anchors.

In the case of the tips shown in FIGS. 4 and 5 (for both PTFE and acetal plastics) it was found that the adhesive bleed holes did not block completely but debris did accumulate on the four external grooves. The debris could easily be removed to allow continued flow of adhesive but it was observed there was some difficulty in detecting whether or not adhesive reached the target site due to the accumulation of debris at the tip.

The invention claimed is:

1. A liquid adhesive application system comprising:
    a liquid applicator configured to hold and discharge a curable liquid adhesive composition, the applicator comprising:
        a receiver body configured to hold the curable liquid adhesive composition;
        a discharge tip with a generally tubular body and having a longitudinal axis, the discharge tip comprising:
            a bore extending the entire length of the discharge tip;
            an inwardly converging inlet at a proximal end of the bore that is adjacent the receiver body and is configured to receive the curable liquid adhesive from the receiver body;
            an outlet opening at a distal end of the bore that is remote from the receiver body and is configured to discharge the curable liquid adhesive composition; and
            a plurality of groove formations formed in an interior wall of the bore and extending from the outlet opening toward the inwardly converging inlet, each of the plurality of groove formations having an arcuate transverse cross-section and a longitudinal axis that is parallel to the longitudinal axis of the discharge tip; and
        a discharge mechanism configured to transfer the curable liquid adhesive composition held by the applicator to the discharge tip for discharge of the curable liquid adhesive composition; and
    the curable liquid adhesive composition,
    wherein the longitudinal axes of said groove formations are equiangularly spaced around the longitudinal axis of the discharge tip, and
    wherein the plurality of groove formations are configured to prevent blockage of the tip, during use, as the curable liquid adhesive composition flows through the bore and is discharged from the discharge tip.

2. The liquid adhesive application system as claimed in claim 1 wherein the bore has an intermediate section of constant cross-section and an outlet section that is downstream of the intermediate section, said groove formations being provided in the outlet section.

3. The liquid adhesive application system as claimed in claim 2 wherein the upstream ends of groove formations are defined by shoulders lying in a plane at right angles to a direction of flow of the curable liquid adhesive composition through the discharge tip.

4. The liquid adhesive application system as claimed in claim 2, wherein a distance from the longitudinal axis of the discharge tip to the interior wall of the bore is greater at each of the plurality of groove formations than a distance from the longitudinal axis of the discharge tip to the interior wall of the bore at the intermediate section.

5. The liquid adhesive application system as claimed in claim 1 wherein the discharge tip comprises a low surface energy material.

6. The liquid adhesive application system as claimed in claim 5 wherein the low surface energy material is a fluorinated polymer or an acetal plastics material.

7. The liquid adhesive application system as claimed in claim 1 adapted to deliver successive droplets of curable liquid adhesive composition.

8. The liquid adhesive application system as claimed in claim 7 comprising a trigger mechanism configured to effect said successive discharge of the droplets.

9. The liquid adhesive application system as claimed in claim 1 having an elongate cannula through which the curable liquid adhesive composition is discharged and at the end of which the discharge tip is mounted.

10. The liquid adhesive application system as claimed in claim 1 for use in laparoscopic surgery.

11. The liquid adhesive application system as claimed in claim 1, wherein a distance from the longitudinal axis of the discharge tip and the interior wall of the bore is greater at each of the plurality of groove formations than at locations between the groove formations.

12. The liquid adhesive application system as claimed in claim 1, wherein the interior wall of the bore at the inlet gradually converges in a direction toward the outlet opening of the discharge tip so that the diameter of the bore is greater at the portion of the inlet adjacent the receiver body than the diameter of the bore at the portion of the inlet furthest from the receiver body.

13. The liquid adhesive application system as claimed in claim 1, wherein the plurality of groove formations radially surround the longitudinal axis of the discharge tip.

14. The liquid adhesive application system as claimed in claim 1, wherein the longitudinal axis of the bore coincides with the longitudinal axis of the discharge tip.

15. A liquid adhesive application system comprising:
a liquid applicator comprising:
   a receiver body;
   a discharge tip with a generally tubular body and having a longitudinal axis, the discharge tip comprising:
      a bore extending the entire length of the discharge tip;
      an inwardly converging inlet at a proximal end of the bore that is adjacent the receiver body and is configured to receive the curable liquid adhesive from the receiver body;
      an outlet opening at a distal end of the bore that is remote from the receiver body and is configured to discharge the curable liquid adhesive composition; and
      a plurality of groove formations formed in an interior wall of the bore and extending from the outlet opening toward the inwardly converging inlet, each of the plurality of groove formations having an arcuate transverse cross-section and a longitudinal axis that is parallel to the longitudinal axis of the discharge tip; and
   a discharge mechanism configured to transfer the curable liquid adhesive composition held by the applicator to the discharge tip for discharge of the curable liquid adhesive composition;
a curable liquid adhesive composition; and
an ampoule that is attachable to the liquid applicator and is configured to hold the curable liquid adhesive composition and discharge the liquid adhesive composition to the receiver body of the liquid applicator,
wherein the longitudinal axes of said groove formations in the discharge tip of the liquid applicator are equiangularly spaced around the longitudinal axis of the discharge tip, and
wherein the plurality of groove formations are configured to prevent blockage of the tip, during use, as the curable liquid adhesive composition flows through the bore and is discharged from the discharge tip.

16. The liquid adhesive application system of claim 15, wherein the curable liquid adhesive composition is a cyanoacrylate adhesive composition.

17. The liquid adhesive application system of claim 15, wherein the curable liquid adhesive composition comprises n-butyl cyanoacrylate.

\* \* \* \* \*